United States Patent
Siegfried et al.

(10) Patent No.: US 11,052,131 B2
(45) Date of Patent: Jul. 6, 2021

(54) METHODS AND PHARMACEUTICAL COMPOSITIONS FOR THE TREATMENT OF KIDNEY CANCER

(71) Applicants: INSERM (Institut National de la Santé et de la Recherche Médicale), Paris (FR); UNIVERSITE DE BORDEAUX, Bordeaux (FR); INSTITUT BERGONIÉ, Bordeaux (FR)

(72) Inventors: Géraldine Siegfried, Pessec (FR); Abdel-Majid Khatib, Pessac (FR); Jean-Luc Hoepffner, Bordeaux (FR); Serge Evrard, Bordeaux (FR)

(73) Assignees: INSERM (INSTITUT NATIONAL DE LA SANTÉ ET DE LA RECHERCHE MÉDICALE), Paris (FR); UNIVERSITE DE BORDEAUX, Bordeaux (FR); INSTITUT BERGONIÉ, Bordeaux (FR)

( * ) Notice: Subject to any disclaimer, the term of this patent is extended or adjusted under 35 U.S.C. 154(b) by 0 days.

(21) Appl. No.: 16/339,931

(22) PCT Filed: Oct. 4, 2017

(86) PCT No.: PCT/EP2017/075134
§ 371 (c)(1),
(2) Date: Apr. 5, 2019

(87) PCT Pub. No.: WO2018/065440
PCT Pub. Date: Apr. 12, 2018

(65) Prior Publication Data
US 2020/0030413 A1 Jan. 30, 2020

(30) Foreign Application Priority Data

Oct. 5, 2016 (EP) .................................. 16306312
May 4, 2017 (EP) .................................. 17305507

(51) Int. Cl.
*A61K 38/22* (2006.01)
*A61P 35/00* (2006.01)
*C07K 14/575* (2006.01)

(52) U.S. Cl.
CPC .............. *A61K 38/22* (2013.01); *A61P 35/00* (2018.01); *C07K 14/575* (2013.01)

(58) Field of Classification Search
CPC ......... A61K 38/16; A61K 38/22; A61P 35/00; C07K 14/575
See application file for complete search history.

(56) References Cited

U.S. PATENT DOCUMENTS

2015/0153365 A1 6/2015 Reversade

FOREIGN PATENT DOCUMENTS

WO WO-2015084264 A1 * 6/2015 ........... C07K 14/575
WO WO 2016/061141 4/2016

OTHER PUBLICATIONS

Cancer Net., Doctor Approved patient information from ASCO, Kidney Cancer: Risk Factors and Prevention Approved by the Cancer.Net Editorial Board, published online Aug. 2019.*
Lena Ho, ELABELA Is an Endogenous Growth Factor that Sustains hESC Self-Renewal via the PI3K/AKT Pathway, Cell Stem Cell 17, 435-447, epub Sep. 2015.*
International Search Report, PCTEP2017/075134, dated Jan. 11, 2018.
Serene C. Chng et al: Il Elabela: A Hormone Essential for Heart Development Signals via the Apelin Receptor, Developmental Cell, vol. 27, No. 6, Dec. 1, 2013 (Dec. 1, 2013) , pp. 672-680, XP055347662, US.
Cheng Deng et al: "Apela Regulates Fluid Homeostasis by Binding to the APJ Receptor to Activate $G_i$ Signaling", Journal of Biological Chemistry, vol. 290, No. 30, Jul. 24, 2015 (Jul. 24, 2015). pp. 18261-18268. XP055351001, US ISSN: 0021-9258. D0I.
Anonymous: "Targeted Therapies for Kidney Cancer". www.cancer.org May 16, 2016 (May 16, 2016). XP002767765, Retrieved from the Internet: URL:https://www.cancer.org/cancer/kidney-cancer/treating/targeted-therapy.html [retrieved on Mar. 3, 2017].

* cited by examiner

*Primary Examiner* — James H Alstrum-Acevedo
*Assistant Examiner* — Erinne R Dabkowski
(74) *Attorney, Agent, or Firm* — Nixon & Vanderhye

(57) ABSTRACT

Disclosed are methods and pharmaceutical compositions for the treatment of kidney cancer. The inventors showed that while Elabela (ELA) is mostly expressed in kidney, its expression is reduced in human kidney cancer. In a xenograft animal model (sub-cutaneous, or sub-capsular injection) Ela inhibits tumor progression. In particular, there is disclosed a method of treating kidney cancer in a subject in need thereof including administering to the subject a therapeutically effective amount of an ELA polypeptide including an amino acid sequence having at least 90% of identity with SEQ ID NO: 1 (QRPVNLTMRRKLRKHNCLQRRCM-PLHSRVPFP) wherein the arginine residue (R) at position 9, 10, 20 or 21 is optionally mutated.

Figure 1:
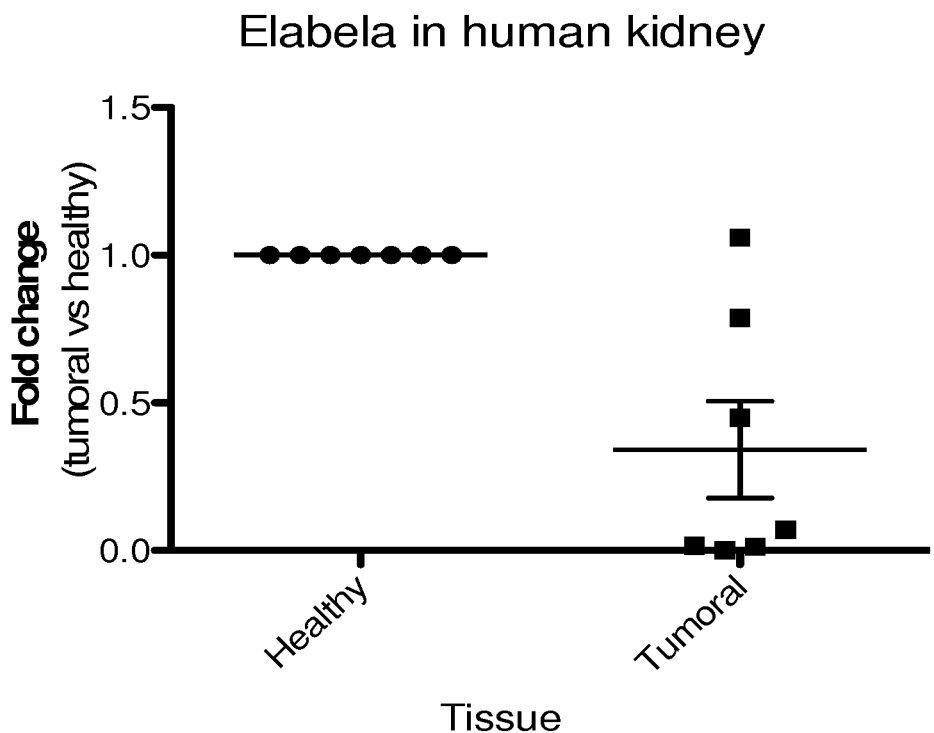

8 Claims, 8 Drawing Sheets
Specification includes a Sequence Listing.

SEQUENCE LISTING

<160> NUMBER OF SEQ ID NOS: 1

<210> SEQ ID NO 1
<211> LENGTH: 32
<212> TYPE: PRT
<213> ORGANISM: Homo sapiens

<400> SEQUENCE: 1

Gln Arg Pro Val Asn Leu Thr Met Arg Arg Lys Leu Arg Lys His Asn

-continued

```
1               5               10              15

Cys Leu Gln Arg Arg Cys Met Pro Leu His Ser Arg Val Pro Phe Pro
            20              25              30
```

METHODS AND PHARMACEUTICAL COMPOSITIONS FOR THE TREATMENT OF KIDNEY CANCER

FIELD OF THE INVENTION

The present invention relates to methods and pharmaceutical compositions for the treatment of kidney cancer.

BACKGROUND OF THE INVENTION

Cancer in the kidney constitutes about 3% of all solid tumors. About 85% of renal tumors are classified as renal cell carcinoma (RCC). Approximately 80% of diagnosed RCC originate from the epithelial cells lining the proximal parts of the kidneys' urine-forming ducts, the tubuli. Due to its appearance under the microscope, this cancer type is known as either renal clear cell carcinoma (RCCC, 65%) or renal papillary cell carcinoma (RPCC, 15%). Renal cell carcinoma (RCC) is the eighth most common malignancy in the United States, with an estimated 62,700 new cases and 14,240 estimated deaths in 2016. Over the last decade, a better understanding of the genetic and metabolic basis of RCC has led to the development of several new targeted therapies to treat metastatic RCC (mRCC). In the setting of metastatic disease, the sequential use of tyrosine kinase inhibitors (TKIs) that target angiogenesis and/or mammalian target of rapamycin (mTOR) inhibitors can result in prolonged progression-free survival and overall survival in the 40 month range. Despite this progress, durable responses to these drugs are exceedingly rare. Thus, there is a need to find alternative treatment strategy. Elabela (ELA) also known as Toddler or Apela is a peptidic hormone that was recently identified as the second ligand of APJ, the apelin receptor. Produced as a precursor of 32 amino-acids (aa), ELA is also found as a 21 aa and 11 aa. ELA is restrictedly expressed in human pluripotent stem cells and adult kidney and prostate.

SUMMARY OF THE INVENTION

The present invention relates to methods and pharmaceutical compositions for the treatment of kidney cancer. In particular, the present invention is defined by the claims.

DETAILED DESCRIPTION OF THE INVENTION

The inventors show that while Elabela (ELA) is mostly expressed in kidney, its expression is reduced in human kidney cancer. In a xenograft animal model (sub-cutaneous, or sub-capsular injection) Ela inhibits tumor progression. These finding identify Ela as a new tumor suppressor gene in kidney.

Accordingly, the first object of the present invention relates to a method of treating kidney cancer in a subject in need thereof comprising administering to the subject a therapeutically effective amount of an ELA polypeptide comprising an amino acid sequence having at least 90% of identity with SEQ ID NO: 1 (QRPVNLTMRRKLRKHN-CLQRRCMPLHSRVPFP) wherein the arginine residue (R) at position 9, 10, 20 or 21 is optionally mutated.

As used herein, the term "kidney cancer" has its general meaning in the art and refer to a cancer that has arisen from the kidney. In some embodiments, the kidney cancer in a renal cell carcinoma. The term "renal cell cancer" or "renal cell carcinoma" (RCC), as used herein, refer to cancer which originates in the lining of the proximal convoluted tubule. More specifically, RCC encompasses several relatively common histologic subtypes: clear cell renal cell carcinoma, papillary (chromophil), chromophobe, collecting duct carcinoma, and medullary carcinoma. Clear cell renal cell carcinoma (ccRCC) is the most common subtype of RCC.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

As used herein, the term mutation has its general meaning in the art and refers to a substitution, deletion or insertion. The term "substitution" means that a specific amino acid residue at a specific position is removed and another amino acid residue is inserted into the same position. The term "deletion" means that a specific amino acid residue is removed. The term "insertion" means that one or more amino acid residues are inserted before or after a specific amino acid residue, more specifically, that one or more, preferably one or several, amino acid residues are bound to an a.-carboxyl group or an a,-amino group of the specific amino acid residue.

In some embodiments, the arginine residue at position at position 9, 10, 20 or 21 is mutated is substituted so that the side chain charge at pH=7,4 is reversed (e.g. negative to positive charge) or is rendered neutral (e.g. negative to neutral charge). In some embodiments, the weight and the hydopathy index remains in the same range.

In some embodiments, the arginine residue (R) at position 9, 10, 20 or 21 is substituted by an amino acid residue selected from the group consisting of alanine (A) and/or serine (S).

According to the invention, the ELA polypeptide of the invention is produced by conventional automated peptide synthesis methods or by recombinant expression. General principles for designing and making proteins are well known to those of skill in the art. The ELA polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The ELA polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides. A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells.

Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In some embodiments, it is contemplated that the ELA polypeptides of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

The second object of the present invention relates to a method of treating kidney cancer in a subject in need thereof comprising administering to the subject a therapeutically effective amount of a nucleic acid molecule which encodes for the ELA polypeptide of the present invention As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid molecule of the present invention is included in a suitable vector, such as a plasmid, cosmid, episome, artificial chromosome, phage or a viral vector. So, a further object of the invention relates to a vector comprising a nucleic acid encoding for a ELA polypeptide of the invention. Typically, the vector is a viral vector which is an adeno-associated virus (AAV), a retrovirus, bovine papilloma virus, an adenovirus vector, a lentiviral vector, a vaccinia virus, a polyoma virus, or an infective virus. In some embodiments, the vector is an AAV vector. As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

By a "therapeutically effective amount" is meant a sufficient amount of the ELA polypeptide or the nucleic acid molecule encoding thereof to prevent for use in a method for the treatment of the disease (e.g. kidney cancer) at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the ELA polypeptide or the nucleic acid molecule (inserted or not into a vector) of the present invention is administered to the subject in the form of a pharmaceutical composition. Typically, the ELA polypeptide or the nucleic acid molecule (inserted or not into a vector) of the present invention may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The ELA polypeptide or the nucleic acid molecule (inserted or not into a vector) of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

A further object of the present invention relates to a method for diagnosing kidney cancer in a subject comprising the steps of:
i) measuring the expression level of Elabela (ELA) in a sample obtained from said subject;
ii) comparing the expression measured at step i) with its predetermined reference value;
iii) concluding that the subject suffers from kidney cancer when the expression level of Elabela (ELA) is lower than its predetermined reference value or concluding that the subject does not suffer from kidney cancer when the expression level of Elabela (ELA) is higher than its predetermined reference value.

The term "diagnosing" as used herein means assessing whether a subject suffers from kidney cancer, or not.

The invention will be further illustrated by the following figures and examples. However, these examples and figures should not be interpreted in any way as limiting the scope of the present invention.

FIGURES

FIG. 1. Reduced expression of Elabela in human cancer kidney. Real time PCR analysis revealed a down-regulation of elabela in kidney tumor tissues while compared to the pseudo-normal tissues derived from the same patient.

Figure 2:
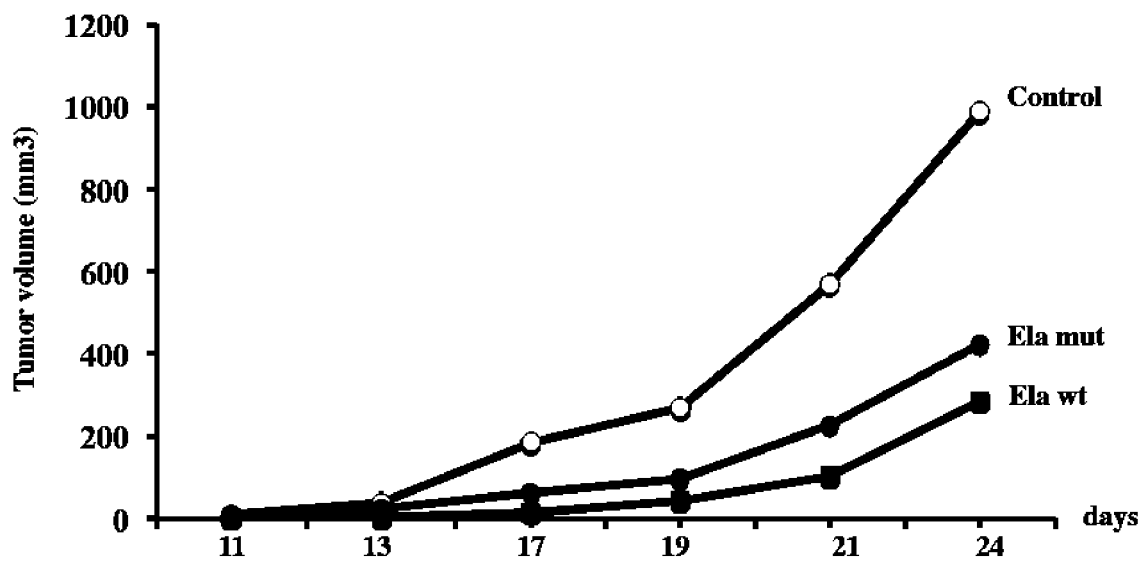

FIG. 2. Effect of Elabela expression in the kidney tumor cells (Renca) on subcutaneous tumor progression. Elabela wild type (ela wt), mutant (Ela mut) or control lentivirus were used to express Ela wt, ela mut in Renca cells prior their inoculation in syngenic mice.

Figure 3:
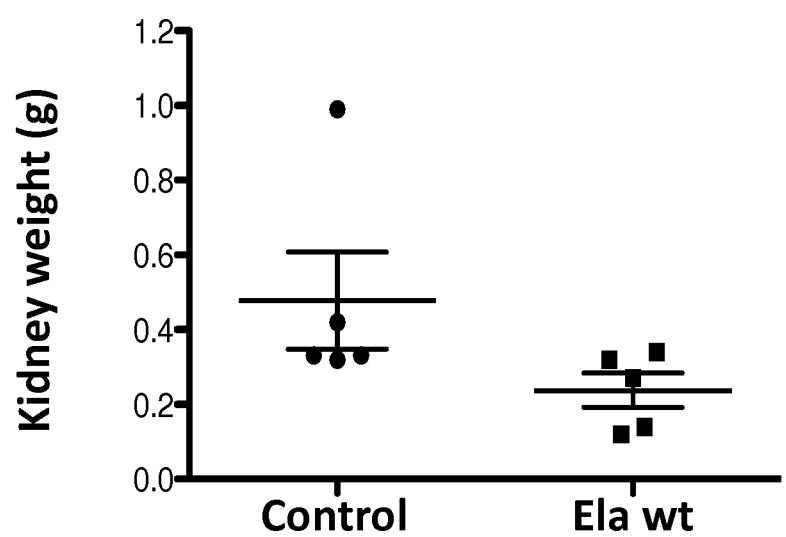

FIG. 3. Effect of Elabela expression in the kidney tumor cells (Renca) on kidney tumor progression. Elabela wild type (ela wt) or control lentivirus were used to express ela wt in Renca cells prior their subcapsular inoculation in syngenic mice.

Figure 4:
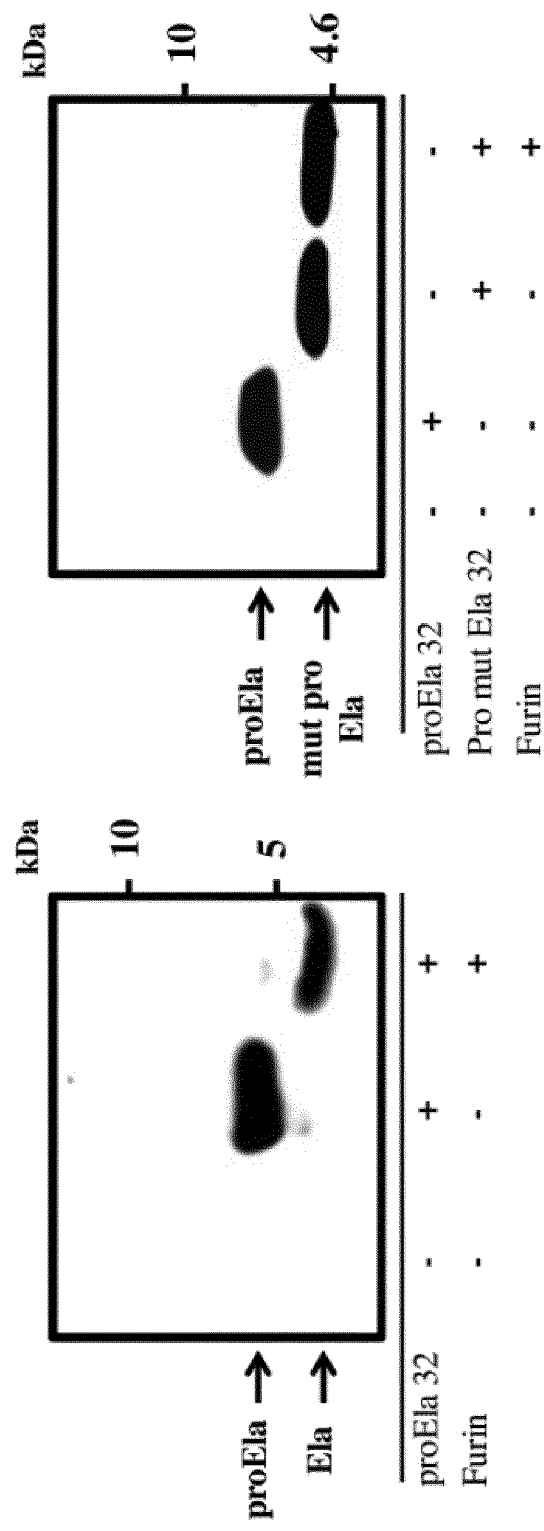

FIG. 4. ProEla processing. Wild type proEla 32 peptide and mut proEla 32 in which the two cleavage sites $R^{31}/R^{32}$ and $R^{42}/R^{43}$ were replaced by $S^{31}/S^{32}$ and $S^{42}/S^{43}$, respectively, were synthesized and incubated with furin ($0.2\times10^{-4}$U) for 4 h. As assessed by western blotting using an anti-Ela antibody, furin processes the wild-type proEla 32 at the corresponding physiological cleavage sites. Incubation of this peptide with furin generates only the Ela 11 aa, suggesting that proEla 32 is cleaved efficiently at the two cleavage sites. Incubation of mut proEla 32 with furin failed to generate any products.

Figure 5:
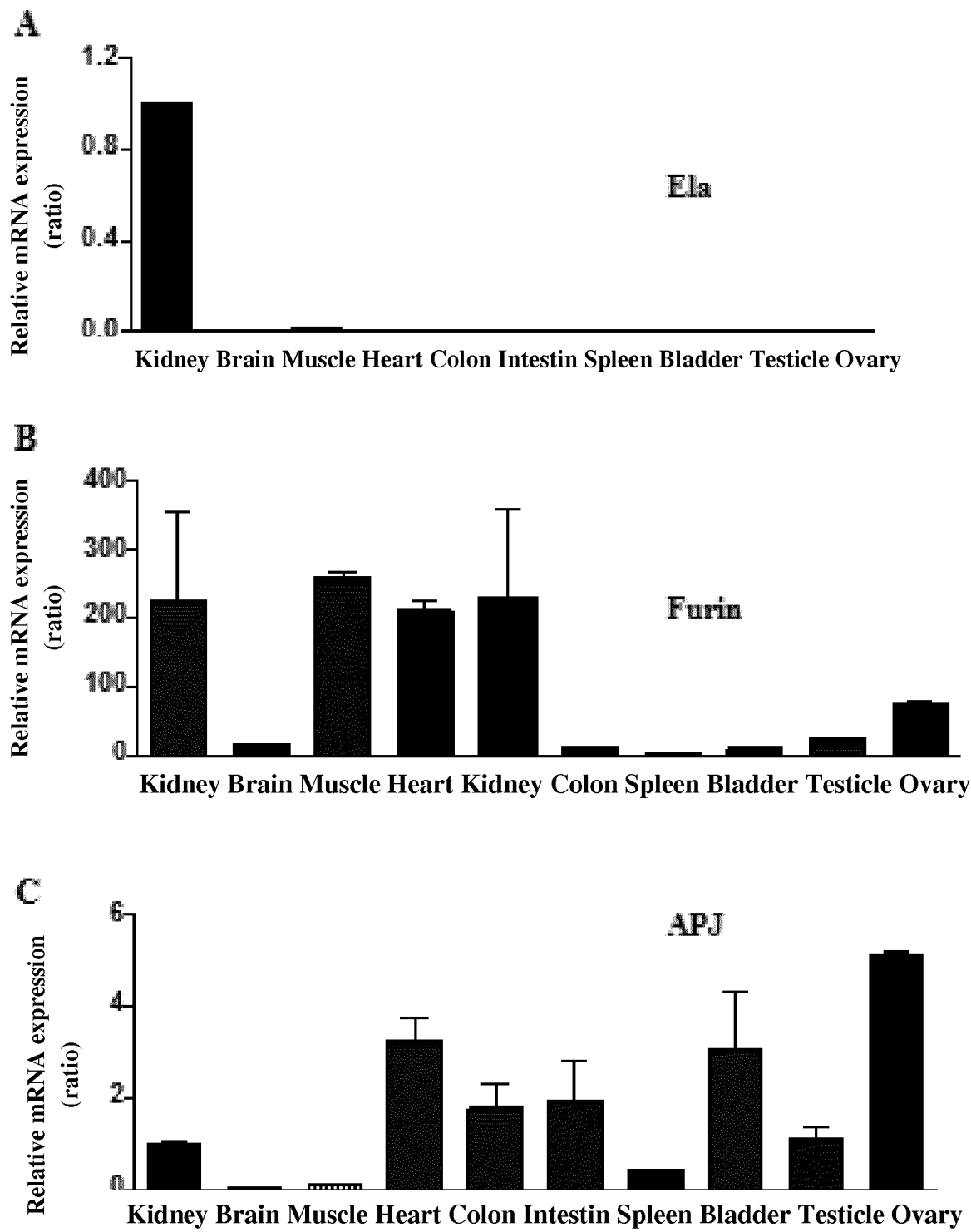

FIG. 5. Expression analysis of Ela, furin and APJ in mouse adult tissues. Total RNA was extracted from indicated tissues and real-time PCR analysis was performed using specific primers for murine Ela (A), furin (B), and APJ (C). Expression of housekeeping gene that was evaluated in each sample was used as endogenous control under the conditions described in the text. Results shown are representative of 3 experiments. For comparison liver (Ela and APJ) or intestine (furin) were assigned a value of 1 depending on the level of the analyzed gene expression. Data are mean±SD (n=3 per group).

Figure 6A:
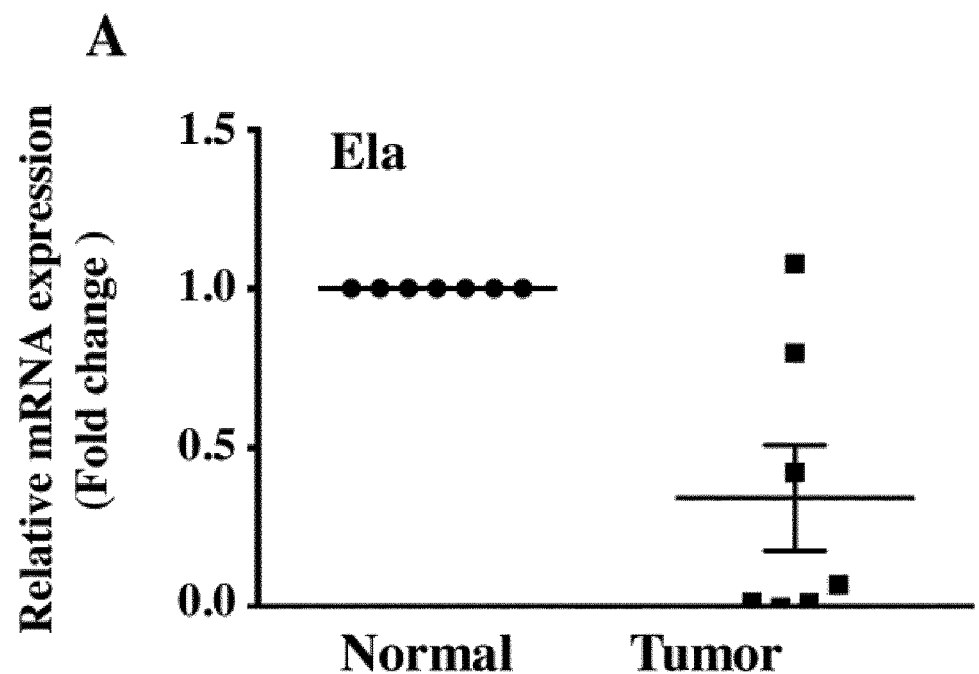
Figure 6B:
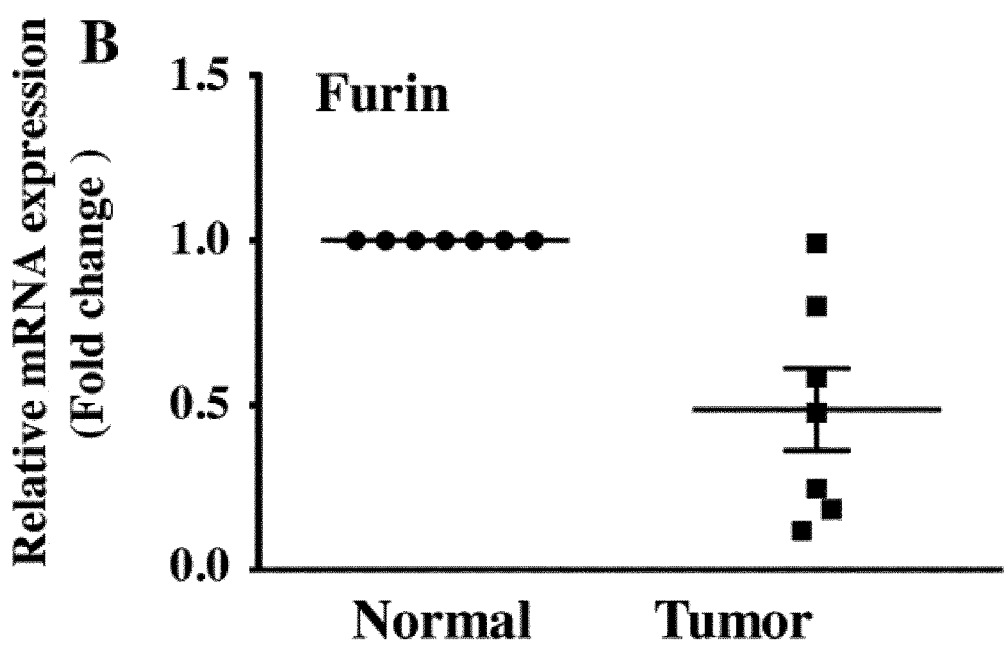
Figure 6C:
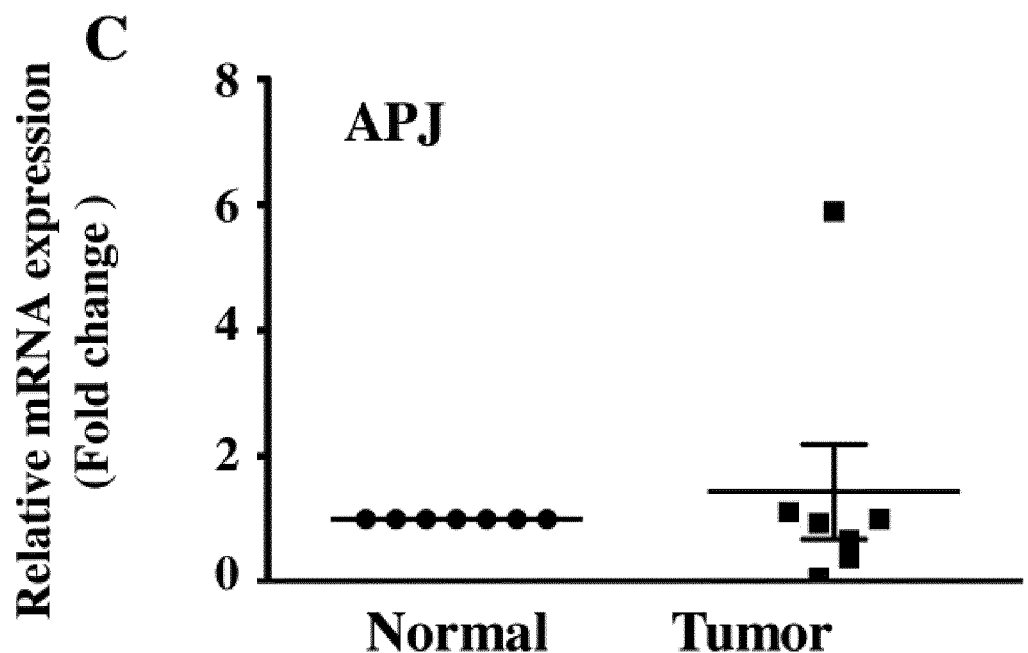

FIG. 6. Expression of Ela, furin and APJ in kidney cancer patients. Total RNA was extracted from tumor and surrounding non-tumor tissue of kidney clinical samples from n=7 patients and real-time PCR analysis was performed using specific primers for human Ela, furin and APJ. Expression of housekeeping gene that was evaluated in each sample was used as endogenous control under the conditions described in the text. Graphs show fold difference in the expression of the indicated transcripts with a value of '1' assigned to normal tissues. Note reduced expression of Ela mRNA in tumor tissues compared to their normal counterparts.

Figure 7A:
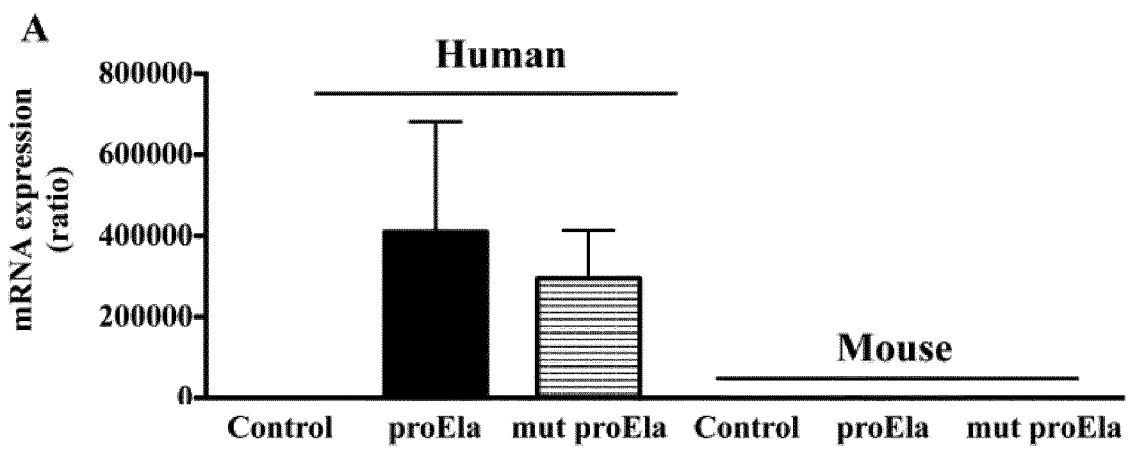

FIG. 7. Inhibition of tumor growth by wild type and mut proEla. The kidney Renca cancer cells (lacking Ela expression) were stably infected with empty lentiviral vector (Control) or the same vector that contains wild type or mutant proEla human construct. The expression of the human wild type and mut proEla in these cells were confirmed at the ARN level using real time PCR and human primers. The use of murine Ela primers was given for comparison (A). Three groups of male syngeneic Balb/c mice were inoculated subcutaneously with $1\times10^5$ of control Renca cells, and the same cells expressing wild-type proEla 32 or mutant proEla 32. The animals were monitored for tumor formation during indicated periods. Note the smaller size of tumors induced by tumor cells expressing wild type proEla or mut ProEla. Wild type proEla 32 inhibited more efficiently tumor growth while compared to mutant pro Ela 32. Results are representative of 2 experiments performed with Renca cells independently infected with indicated lentiviral vectors. Values are mean±SEM (n=6 per group). ***$P<0.001$.

Figure 8:
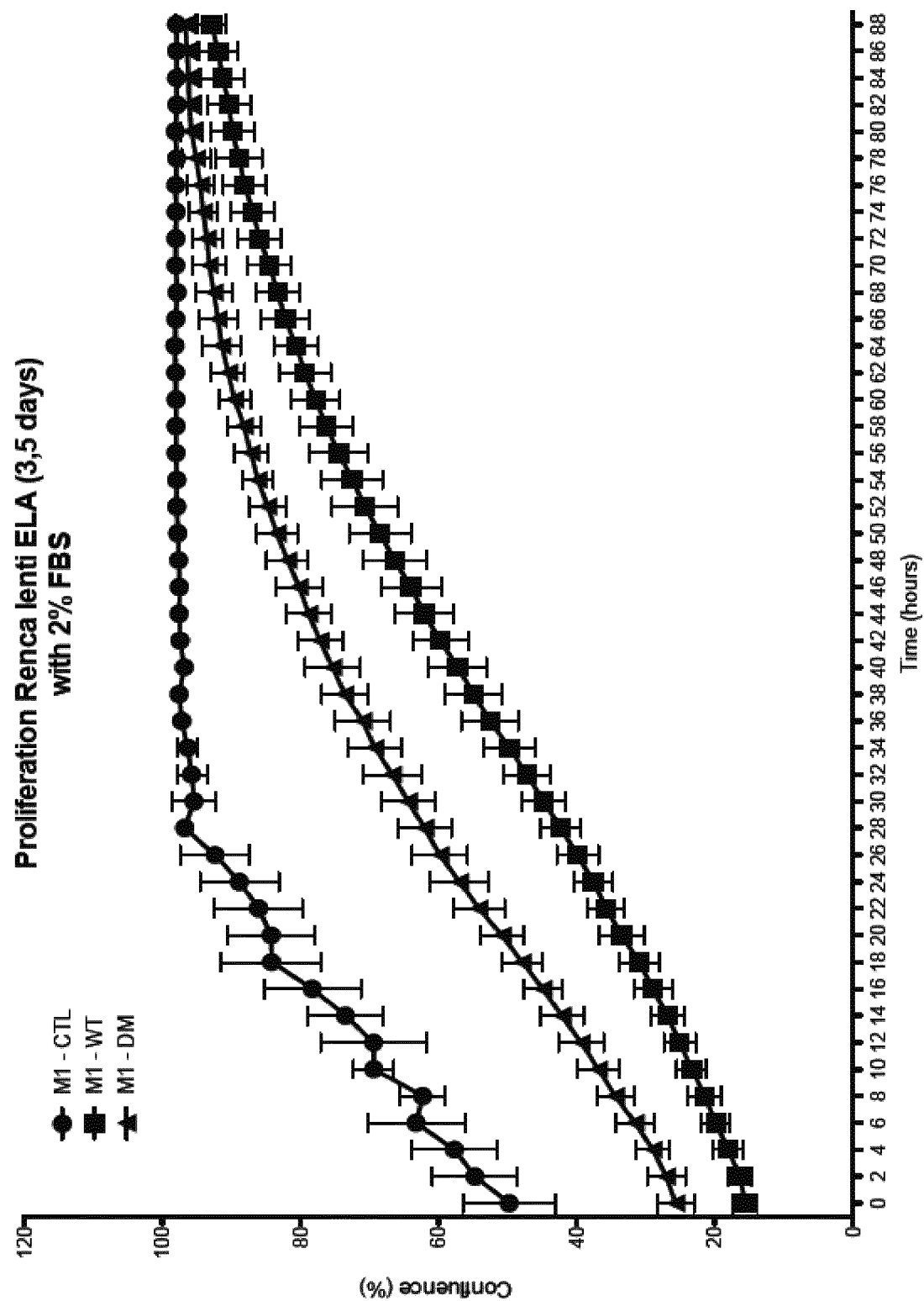

FIG. 8. RENCA (20,000 cells 4 cells/well) cells were plated in 96-well plates, proliferation assay was performed using the IncuCyte ZOOM™ live cell imaging system (Essen BioScience, MI USA). This system measures cell density. Cells are routinely propagated in RPMI 1640 medium (Life Technologies) in 2% foetal calf serum at 37° C. Cells are regularly screened for *Mycoplasma* (ATCC). The plate is placed into the IncuCyte ZOOM™ apparatus and images of the collective cell spreading are recorded every 2 hours for a total duration of 50 hours.

EXAMPLE 1

Elabela (ELA) also known as Toddler or Apela is a peptidic hormone that was recently identified as the second ligand of APJ, the apelin receptor. Produced as a precursor of 32 amino-acides (aa), ELA is also found as a 21 aa and 11 aa. Our results show that Ela is mostly expressed in kidney, and its expression is reduced in human kidney cancer (FIG. 1). In a xenogreff animal model (sub-cutaneous, or sub-capsular injection) Ela inhibits tumor progression (FIGS. 2 and 3). Beside, we have generated a mutant ELA polypeptide wherein the arginine residues at position 9, 10, 20 and 21 were substituted by a serine residue. We show that the mutant ELA polypeptide is also capable of inhibiting tumor progression (FIG. 2). These finding identify Ela as a new tumor suppressor gene in kidney.

EXAMPLE 2

Material and Methods
Patient Samples
Fresh samples and their corresponding normal tissues were obtained from human kidney tumors. All patients provided written informed consent. Patient material was de-identified and the national research ethics review committee in France approved the study protocol. After surgery, tissue specimens were immediately transferred on ice and snap-frozen in liquid nitrogen until used for RNA extraction.

Lentiviral Vectors Production, Cell Infection and Culture

Wild type and mutant proEla (processing sites $R^{31}/R^{32}$ and $R^{42}/R^{43}$ were replaced by $S^{31}/S^{32}$ and $S^{42}/S^{43}$ aa) were cloned into a multicistronic self-inactivating lentiviral vector containing a tdTomato reporter gene (pRRLsin-MND-hPGK-tdTomato-WPRE), under the control of the myeloproliferative sarcoma virus enhancer. All constructs were verified by sequencing. Lentiviral vectors construction and production were performed by the "Vect'UB" facility of the TMB-Core of Bordeaux University. VSV-G pseudotyped lentivectors were produced by triple transient transfection in HEK293T cells and were concentrated by ultrafiltration (Vivaspin 20, Sartorius Biotech SA, USA). Viral titers of pLV lentivectors were determined by transducing HEK293T cells with serial dilutions of viral supernatant and tdTomato expression was quantified 5 days later by flow cytometry analysis. The day of the infection, the murine kidney adenocarcinoma Renca cells ($5 \times 10^4$ cells/well) were seeded in twenty-four-well plate with polybrene at 8 µg/ml. Lentivirus encoding for wild type proEla, mutant proEla, or only tdTomato, was added to medium at MOI 10 (Multiplicity Of Infection). Cell infection rates were observed 72 hours later using a fluorescent microscope. Renca cells were maintained in RPMI1640 medium supplemented with 10% FCS, 100 units/ml penicillin/streptomycin and 2 mM L-Glutamine.

Real-Time Polymerase Chain Reaction Analysis

Total RNA from human samples was extracted using the NucleoSpin RNA kit (Macherey-Nagel) according to the manufacturer's instructions. Total RNA from mouse samples were extracted using TRI Reagent (MRC Inc., US) according to the manufacturer's instructions. One µg of total RNA was subjected to cDNA synthesis using the high capacity cDNA reverse transcription kit (Applied Biosystems, Courtaboeuf, France). The RNA quality for human samples was checked using the Agilent RNA 6000 Nano kit according to the manufacturer's instructions (Agilent). The relative quantification of specific mRNAs was performed by real-time PCR using the StepOnePlus™ Real-Time PCR System (Applied Biosystems, Courtaboeuf, France), PCR Master Mix (Eurogentec) and specific primers, according to the manufacturer's instructions. The conditions for the reaction were as follows for SYBR Green qPCR: 10 minutes at 95° C., for 40 cycles 15 seconds at 95° C., 60 seconds at 60° C., and then 15 minutes at 95° C., 60 seconds at 60° C. and 15 minutes at 95° C.; and for Taqman qPCR: 2 minutes at 50° C., 10 minutes at 95° C., for 40 cycles 15 seconds at 95° C. and 60 seconds at 60° C. GAPDH, HPRT1 or S16 housekeeping genes were used as endogenous controls for human or mouse cells and tissues, as previously described (Scamuffa et al., 2008).

Peptide Synthesis and In Vitro Enzymatic Digestion

Ela 11, wild type proEla 32 and mutant proEla 32 peptides were synthesized by Cliniscences. Ela peptides were digested with furin for 4 h as previously described (Sfaxi et al., 2014, Scamuffa et al., 2008) and were subjected to Western blotting analysis.

Western Blotting Analysis

The generated in vitro enzymatic digestion products were subjected to SDS-polyacrylamide gel electrophoresis in 13% gels. The primary antibody used was an anti-Ela 11 (Eurogentec). Horseradish peroxidase-conjugated secondary antibody and enhanced chemiluminescence (ECL+Plus, Amersham) were used for primary antibody revelation according to the manufacturers' instructions using a Chemiluminescence imaging system (GeneGnome, Syngene) (Sfaxi et al., 2014, Scamuffa et al., 2008).

Receptor Internalization Assay

HEK293A cells stably expressing human GFP-APJ fusion protein were serum starved for 24 hours, and treated for 30 minutes with 1 µM Ela 11, wild type proEla 32 or mutant proEla 32 peptide. Cells were fixed with 4% paraformaldehyde for 10 minutes at room temperature and APJ receptor internalization was analyzed using a Nikon epifluorescence microscopy.

ERK, AKT and P70 Activation Analysis

HEK293A over-expressing human GFP-APJ fusion protein cells were maintained in serum-free media condition for 24 and were incubated with (1 µM) or without Ela 11, wild type proEla or mutant proEla for 5, 15 and 30 min at 37° C. Cells were lysed in RIPA buffer (150 mM NaCl, 50 mM Tris, 1 mM EDTA, 1% NP40, 0.25% sodium deoxycholate, pH8) and were subjected to SDS-PAGE on 12% gels. Cell lysates were analyzed by western blotting for ERK, AKT and P70 phosphorylation using an anti-phospho-ERK; anti-phospho-AKT and anti-phospho-P70 (Cell Signaling), respectively. The blots were stripped and reprobed with ERK, AKT or P70 (Cell Signaling) for data normalization. Primary antibodies were visualized using horseradish peroxidase-conjugated secondary antibodies (Amersham), and signals were detected using ECLPlus chemiluminescence system according to the manufacturers' instructions (Amersham).

mTOR Signalling Pathway

RENCA cells overexpressing lentivirus encoding for wild type proEla, mutant proEla, or only tdTomato, were maintained in serum free media for different time. Cells were lysed in RIPA buffer (150 mM NaCl, 50 mM Tris, 1 mM EDTA, 1% NP40, 0.25% sodium deoxycholate, pH8) and were subjected to SDS-PAGE on 12% gels. Cell lysates were analyzed by western blotting for LC3, NFkB, Erk1/2, AKT, S6K or actin using anti phosphor NFkB, anti-phospho Erk, anti-phospho-Akt, anti-phospho S6K. The blots were stripped and reprobed with ERK, AKT or P70 (Cell Signaling) for data normalization. Primary antibodies were visualized using horseradish peroxidase-conjugated secondary antibodies (Amersham), and signals were detected using ECLPlus chemiluminescence system according to the manufacturers' instructions (Amersham).

Tumorigenicity Assay 7- to 8-week-old Balb/c mice from Janvier Laboratories were housed in ventilated carousel racks and provided with sterile food and drink water. Animal Housing and Experiment Board of the French government approved all the mouse experiments reported herein. To assess the effect of wild type proEla and mutant proEla expression on Renca cells ability to induce tumor growth, $1 \times 10^5$ Renca cells or the same cells stably expressing wild type proEla or mutant proEla were injected subcutaneously into syngeneic Balb/c mice. Tumor formation was monitored every 2-3 days, and mice were sacrificed in the end of the experiments. Tumor volume was calculated as previously described (Sfaxi et al., 2014).

Wound Healing Assay

Renca cells were cultivated until sub-confluency. A scratch is realized with a tip on each well and the wound healing is observed after 8 or 24 h after serum starvation.

Statistics

All the data was expressed as mean±standard deviation (SD) and the statistical analysis was performed using Graphpad Prism 5.0 (GraphPad Software Inc., San Diego, Calif.). p-values<0.05 were considered significant.

Results

ProEla 32 Processing by the Proprotein Convertase Furin.

The cDNA structure of human ELA predicts an 54 amino acids (aa) pre-proEla. Following the removal of the 22 aa of the signal peptide the hormone is released as proEla of 32 aa. The presence of two basic amino acid motifs $R^{31}/R^{32}$ and $R^{42}/R^{43}$ in proEla 32 suggests the participation of PCs in its processing (data not shown). Through Genbank databases we found that the proEla sequence is highly conserved, particularly around the PC-like cleavage sites RX(K/R)RQ (data not shown). To study the importance of the proteolytic maturation of preEla 32 by the PCs in the mediation of its function we first assessed experimentally proEla 32 processing by furin using an in vitro digestion assay. For this matter, we synthesized wild type proEla 32 aa which contains the processing sites of proEla ($R^{31}/R^{32}$ and $R^{42}/R^{43}$) and a mutant peptide proEla 32 which the processing sites were mutated to $S^{31}/S^{32}$ and $S^{42}/S^{43}$, respectively. As illustrated in FIG. 4, incubation of wild type proEla with recombinant human furin ($0.2\times10^{-4}$U) generated predominantly the mature Ela 11 aa, suggesting that the $R^{31}/R^{32}$ and $R^{42}/R^{43}$ sites are cleaved efficiently and simultaneously by furin, avoiding the generation of the intermediate ELA 22 aa form under these conditions. In contrast, incubation of the mutant peptide ProEla 32 ($S^{31}/S^{32}$ and $S^{42}/S^{43}$) with furin failed to generate any mature Ela products, supporting the specific processing of proEla by the PCs at the $R^{31}/R^{32}$ and $R^{42}/R^{43}$ physiological cleavage sites.

Expression Analysis of Ela, Furin and APJ in Adult Mice and Kidney Cancer Patients Tissues.

Real time PCR analysis of various adult mice tissues revealed that while furin and APJ are expressed in all the analyzed tissues, Ela is mainly expressed in the kidney (FIG. 5). The coordinated expression of Ela, its receptor APJ and its converting enzyme furin in normal mice kidney epithelium directed us to investigate the level extent of these genes expression in human kidney cancers and to evaluate the role of Ela and its processing in this disease. Thereby, using real time PCR analysis of tissues obtained from patients with kidney cancer revealed omnipresent expression of Ela, APJ and furin (FIG. 6). While compared to normal tissues, reduced expression of Ela and furin was detected in the analyzed kidney cancer tissue patients. Of the 7 patient tissues analyzed Ela was down-regulated in 6 patients.

APJ Internalization and Ela Peptides

Ligand-induced receptor internalization is a cellular response of APJ to ligand binding and its activation. To investigate whether mature ELA 11, wild type and mutant pro Ela 32 will induce APJ internalization, we expressed in stable manner APJ as a fusion protein with enhanced green fluorescent protein (GFP-APJ, data not shown) through lentiviral infection in HEK293 cells and examined its intracellular localization in response to indicated Ela peptides. At the basal level, the fusion protein was mainly localized at the cell surface. Following Ela peptide treatments, large vesicles were formed in the cytoplasm after 30 min, suggesting that all the Ela peptide forms are able to activate the APJ receptor and mediate its internalization. Similarly treatment of cells with Ela 11 and mut proEla 32 or wild type proEla and mut proEla also induced APJ internalization.

ERK, AKT and p70 Activation Analysis

To evaluate the importance of proEla processing in the mediation of ERK, AKT and p70 signaling, we treated HEK293 cells expressing APJ with wild type, mut proEla 32 or mature Ela 11. All these Ela peptides (1 µM) were able to induce the phosphorylation of ERK within 5 min of treatment (data not shown). This effect was reduced after 15 min as revealed by Western analysis. Interestingly, under the same conditions, the effect of wild type proEla on ERK activation was higher as compared to mut proEla and Ela 11 effect (data not shown). Analysis of AKT activation revealed that all the tested peptides induced lower AKT activation while compared to their effect on ERK activation. A weak visible phosphorylation of AKT was seen after 5 min that peaked at about 15 min and decreased thereafter (data not shown). Similarly analysis of the AKT downstream effector P70s6K revealed that 1 µM of all the tested peptides failed to induce significant effect under the same conditions (data not shown).

mTOR Signaling Pathway

To evaluate the role of Elabela on kidney cancer progression, we used RENCA cells expressing elabela or elabela mutated at the furin site. Cells wera starved of serum for 1, 3, 6, 12 or 24 hours and the effect of Elabela on the mTOR pathway was observed by lookind at the phosphorylation or nfkB, Erk1/2, akt, or S6K.

The expression of either WT and MUT versions of ELABELA in RENCA cells during serum starvation induced:

1. A block in the induction of autophagy, as estimated by reduced LC3II levels.
2. A sustained activation of mTORC1 pathway, as determined by the sustained S6K and S6 phosphorylation.
3. An enhanced inhibition of ERK signaling, as determined by an increase in ERK phosphorylation.
4. No effect in mTORC2 signaling as determined by P(473) AKT.
5. No effect in PI3K signaling as determined by P(308)AKT.
6. No effect in NFkB signaling.

Role of Ela and proEla Processing in Tumorigenesis.

Figure 7B:
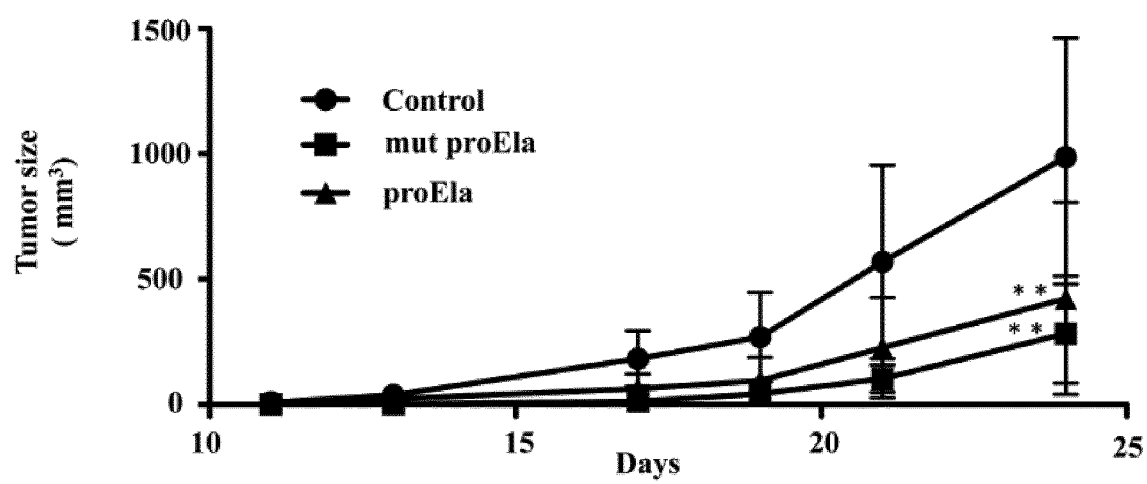

To investigate the role of wild type and mutant proEla 32 on tumor progression, we took advantage of the murine kidney Renca cancer cells that lack Ela expression and the use of the lentiviral vectors pRRLsin-MND-hPGK-tdTomato-WPRE to deliver and stably express wild type and mutant proEla 32 in these cells. Prior to analysis, Renca cancer cells stably expressing wild-type and mutant human proEla were assessed for the expression of these constructs using real time PCR (FIG. 7A) and by the presence of the tdTomato fluorescent protein (data not shown). Three groups of male syngeneic Balb/c mice were inoculated subcutaneously with $1\times10^5$ of control cells, and the same cells expressing wild-type proEla 32 or mutant proEla 32. As illustrated in FIG. 7B, the expression of wild type or mutant proEla in these tumor cells reduced significantly tumor growth while compared with control cells expressing empty vector. Expression of wild type wild type proEla 32 seemed to inhibit more efficiently tumor growth while compared to mutant proEla 32. These datas are confirmed by wound healing experiment (data not shown). Elabela inhibits wound healing of Renca cells in vitro and also in FIG. 8 for cells proliferation assay. Elabela inhibits renca cells proliferation.

Discussion

The ubiquitous expression of furin and the presence of a dibasic cleavage motif in Ela precursor (proEla 32) suggests that the PCs are protease candidates for proEla processing (data not shown). In the current study we demonstrate that the PCs (furin) are implicated in the proteolytic processing of proEla at two cleavage sites namely $R^{31}/R^{32}$ and $R^{42}/R^{43}$. In our model, the cleavage sites of proEla were confirmed by mutagenesis and in vitro enzymatic digestion of the wild type and mutant proEla peptides (FIG. 4). However although the cleavage of the proEla (32 aa) at these two cleavage sites suppose to generate Ela 22 and Ela 11 peptide forms, only the Ela 11 form was detected under these conditions suggesting the possible rapid conversion of Ela 22 to Ela 11 in the presence of furin (FIG. 4). Analysis of various adult mice tissues showed the co-expression of Ela, it receptor APJ and furin mRNA's (FIG. 5) reinforcing the functional link between the three. These data are further corroborated by the striking temporal correlation between the expression of Ela, APJ and furin during embryonic development (Scamuffa et al., 2006, Helker et al., 2015), suggesting a key role of these genes during these processes. Accordingly previous reports indicate that the ELA mutant phenotype is similar to the APJ mutants in zebrafish, and inactivation of the fur locus by homologous recombination in mouse causes embryonic death shortly after e10.5 (Scamuffa et al., 2006). Therefore suggests that ELA, its converting protease furin and receptor APJ are involved in biological functions required for normal embryonic devolvement. However, in this study we found that the inhibition of proEla precursor processing failed to affect significantly its biological function. Indeed, ELA was originally found well conserved in vertebrates (Pauli et al., 2014, Chng et al., 2013), particularly around the PCs cleavage sites (data not shown) and described as a specific ligand for APJ suggesting a functional conservation of the ELA-APJ pathway in mammalians. Lately Ela was reported to mediate other functions trough its interaction with the heterogeneous nuclear ribonucleoprotein L (hnRNPL), an inhibitory regulator of p53 (Li et al., 2015), raising questions about the mechanism(s) that determine the distinct effects of Ela in vitro and in vivo. To investigate the importance of proEla processing and functionality and its relationship to APJ signaling, we generated HEK cells stably expressing GFP-APJ. We demonstrated that synthetic human mature ELA, wild type proEla and mutant proEla peptides cause the internalization of human APJ (data not shown) and that activation of APJ by these peptides results in significant activation of ERK (data not shown) thus establishing that processed or unprocessed ELA are able to activate APJ under these conditions. Compared to ERK activation, all the tested Ela peptides failed to induce significant AKT and its downstream effector P70 activation (data not shown). Previously, APJ and furin over-expression were linked to various cancers and metastasizing tumors. Analysis of the levels of Ela expression in normal and tumor tissue samples from 7 patients with kidney cancer demonstrated that Ela was down-regulated in 6/7 patients, suggesting the potential tumor suppressor action of Ela (FIG. 6). Thereby, to directly investigate the biological role of Ela and proEla processing in tumor growth, we took advantage of the murine kidney Renca cells that lack Ela expression and induces tumors in Balb/c mice. we found that the expression of wild type or mutant proEla in these cells inhibited tumor cells ability to induce tumor growth in mice (FIG. 7B). How Ela is involved in the repression of tumor growth is not presently clear, but several mechanisms may be postulated. Differences in the ability of Ela peptides to induce AKT and ERK activation may be a contributing factor. Previously, the outcome of ERK activation was found to depend on its expression levels and activity. While in normal cells, high levels of ERK activation induces cellular senescence, reduced ERK activity was found to rescue cells from senescence and facilitated their transformation by the ras oncogene, suggesting a tumor suppressor role for the ERK signaling (Deschênes-Simard et al., 2013). The ERK-mediated senescent was reported to involve degradation by the proteasome of various proteins required for different biological functions including cell proliferation and migration, RNA metabolism, and cell signaling. Accordingly, the phospho-ERK levels are very low in various human cancers including mammary carcinomas (Milde-Langosch et al., 2005), brain (Mawrin et al., 2003, Mawrin et al., 2005), prostate (Malik et al., 2002), pancreatic (Yip-Schneider et al., 2001) and kidney tumors (Lee et al., 2009, Svensson et al., 2009). Similarly, patients with high ERK levels correlated with good prognosis, a less aggressive phenotype (Milde-Langosch et al., 2005; Lee et al., 2009, Svensson et al., 2009), had better survival and responded better to treatment (Chadha et al., 2006). In contrast several advanced cancers were found to correlate with low phospho-ERK and high AKT levels (Malik et al., 2002, Deng et al., 2015). Indeed; the AKT pathway is the most commonly disrupted signaling pathway in human cancers (Millis et al., 2016) and AKT pathway aberrations have been identified in up to 40% of all tumor types. Numerous compounds that inhibit the AKT pathway at all levels are now in clinical development, including those that directly targeting AKT (Yap et al., 2008). These studies suggest that some of the tumor suppressor functions of the ERK pathway but not AKT could be reactivated in cancer patients. Based on the ability of Ela to induce high ERK and low AKT activity may constitute a potential strategy for the treatment of kidney cancer. In conclusion, we identify Ela as potential new tumor suppressor gene and describe a plausible mechanism linking Ela ability to ERK activation and tumor growth inhibition.

In RENCA cells, ELABELA (both WT and MUT) induced mTORC1 activation by inhibiting S6K phosphorylation, involved in the mTORC1 pathway, ans as mTORC1 is a direct inhibitor of mTOR, this effect acts also on ERK pathway (data not shown).

We concluded that Elabela acts via mTOR as a tumor suppressor.

REFERENCES

Throughout this application, various references describe the state of the art to which this invention pertains. The disclosures of these references are hereby incorporated by reference into the present disclosure.

The invention claimed is:

1. A method of treating kidney cancer in a subject in need thereof comprising administering to the subject already afflicted or diagnosed with kidney cancer, a therapeutically effective amount of an Elabela (ELA) polypeptide or a nucleic acid encoding thereof wherein the ELA polypeptide comprises SEQ ID NO: 1 (QRPVNLTMRRKLRKHN-CLQRRCMPLHSRVPFP) and wherein the arginine residue (R) at at least one of positions 9, 10, 20 and 21 is optionally mutated.

2. The method of claim 1 wherein the subject suffers from a renal cell carcinoma.

3. The method of claim 2 wherein the renal cell carcinoma is selected from the group consisting of a clear cell renal cell carcinoma, a papillary renal cell carcinoma, a chromophobe renal cell carcinoma, a collecting dust carcinoma and a medullary carcinoma.

4. The method of claim 2 wherein the renal cell carcinoma is a clear cell renal cell carcinoma.

5. The method of claim 1 wherein the arginine residue (R) at position 9, 10, 20 or 21 is substituted by an Alanine residue (A) or a Serine residue (S).

6. The method of claim 1 wherein the nucleic acid molecule is included in a suitable vector, such as a plasmid, cosmid, episome, artificial chromosome, phage or a viral vector.

7. The method of claim 1 wherein the arginine residue (R) at position 9, 10, 20 and 21 is substituted by a Serine residue (S).

8. A method of treating kidney cancer in a subject in need thereof comprising administering to the subject already afflicted or diagnosed with kidney cancer, a therapeutically effective amount of an Elabela (ELA) polypeptide or a nucleic acid encoding thereof wherein the ELA polypeptide comprises an amino acid sequence having at least 90% of identity with SEQ ID NO: 1 (QRPVNLTMRRKLRKHN-CLQRRCMPLHSRVPFP) wherein the arginine residue (R) at position 9, 10, 20 or 21 is optionally mutated.

* * * * *